United States Patent
Chen et al.

(10) Patent No.: US 10,398,414 B2
(45) Date of Patent: *Sep. 3, 2019

(54) ANALOG-TO-DIGITAL DRIVE CIRCUITRY HAVING BUILT-IN TIME GAIN COMPENSATION FUNCTIONALITY FOR ULTRASOUND APPLICATIONS

(71) Applicant: Butterfly Network, Inc., Guilford, CT (US)

(72) Inventors: Kailiang Chen, Branford, CT (US); Keith G. Fife, Palo Alto, CA (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/243,546

(22) Filed: Jan. 9, 2019

(65) Prior Publication Data
US 2019/0142393 A1    May 16, 2019

Related U.S. Application Data

(63) Continuation of application No. 15/263,939, filed on Sep. 13, 2016, now Pat. No. 10,231,713.

(51) Int. Cl.
*A61B 8/08* (2006.01)
*A61B 8/00* (2006.01)
(Continued)

(52) U.S. Cl.
CPC .............. *A61B 8/56* (2013.01); *A61B 8/5207* (2013.01); *A61B 8/54* (2013.01); *G01S 7/52033* (2013.01);
(Continued)

(58) Field of Classification Search
CPC .......... A61B 8/56; A61B 8/54; A61B 8/5207; H03M 1/0617; H03M 1/1245; H03M 1/129; G01S 7/52033
See application file for complete search history.

(56) References Cited

U.S. PATENT DOCUMENTS 4,810,949 A   3/1989  Schiemenz et al.
4,852,576 A   8/1989  Inbar et al.
(Continued)

FOREIGN PATENT DOCUMENTS

WO   WO 2010/055427 A1   5/2010
WO   WO 2011/163475 A1   12/2011

OTHER PUBLICATIONS

International Preliminary Report on Patentability dated Mar. 28, 2019 in connection with International Application No. PCT/US2017/049024.

(Continued)

*Primary Examiner* — Daniel Pihulic
(74) *Attorney, Agent, or Firm* — Wolf, Greenfield & Sacks, P.C.

(57) ABSTRACT

A time gain compensation (TGC) circuit for an ultrasound device includes a first amplifier having an integrating capacitor and a control circuit configured to generate a TGC control signal that controls an integration time of the integrating capacitor, thereby controlling a gain of the first amplifier. The integration time is an amount of time an input signal is coupled to the first amplifier before the input signal is isolated from the first amplifier.

30 Claims, 11 Drawing Sheets

(51) Int. Cl.
*H03M 1/06* (2006.01)
*H03M 1/12* (2006.01)
*G01S 7/52* (2006.01)

(52) U.S. Cl.
CPC ....... *H03M 1/0617* (2013.01); *H03M 1/1245* (2013.01); *H03M 1/129* (2013.01)

(56) References Cited

U.S. PATENT DOCUMENTS

| | | | |
|---|---|---|---|
| 5,233,305 | A | 8/1993 | Nishizawa et al. |
| 5,263,092 | A | 11/1993 | Jang |
| 5,351,030 | A | 9/1994 | Kobayashi et al. |
| 5,408,199 | A | 4/1995 | Nagano et al. |
| 5,482,044 | A | 1/1996 | Lin et al. |
| 5,757,220 | A | 5/1998 | Murden et al. |
| 5,955,670 | A | 9/1999 | Goodman et al. |
| 5,963,882 | A | 10/1999 | Viertl et al. |
| 6,163,288 | A | 12/2000 | Yoshizawa |
| 6,229,375 | B1 | 5/2001 | Koen |
| 6,693,491 | B1 | 2/2004 | Delano |
| 6,828,873 | B2 | 12/2004 | Ludwig et al. |
| 7,253,700 | B1 | 8/2007 | Chiu |
| 7,313,053 | B2 | 12/2007 | Wodnicki |
| 8,076,995 | B2 | 12/2011 | Chiu |
| 8,330,536 | B1 | 12/2012 | Quinn |
| 8,514,007 | B1 | 8/2013 | Ahmed et al. |
| 8,653,890 | B1 | 2/2014 | Ahmed et al. |
| 8,852,103 | B2 | 10/2014 | Rothberg et al. |
| 9,100,046 | B2 | 8/2015 | Granger-Jones |
| 9,229,097 | B2 | 1/2016 | Rothberg et al. |
| 9,327,142 | B2 | 5/2016 | Rothberg et al. |
| 9,351,706 | B2 | 5/2016 | Rothberg et al. |
| 9,444,432 | B2 | 9/2016 | Shrivastava et al. |
| 9,543,925 | B2 | 1/2017 | Hau |
| 10,082,488 | B2 | 9/2018 | Chen et al. |
| 10,231,713 | B2 * | 3/2019 | Chen ........................ A61B 8/56 |
| 2002/0180520 | A1 | 12/2002 | Ueno et al. |
| 2007/0030070 | A1 | 2/2007 | Brueske et al. |
| 2007/0069934 | A1 | 3/2007 | Mills et al. |
| 2007/0090877 | A1 | 4/2007 | Bagheri et al. |
| 2007/0242567 | A1 | 10/2007 | Daft et al. |
| 2009/0250729 | A1 | 10/2009 | Lemmerhirt et al. |
| 2010/0063399 | A1 | 3/2010 | Walker et al. |
| 2010/0152587 | A1 | 6/2010 | Haider et al. |
| 2010/0164656 | A1 | 7/2010 | Chiu |
| 2010/0317972 | A1 | 12/2010 | Baumgartner et al. |
| 2011/0133841 | A1 | 6/2011 | Shifrin |
| 2011/0148682 | A1 | 6/2011 | Rigby et al. |
| 2013/0043962 | A1 | 2/2013 | Granger-Jones |
| 2013/0120061 | A1 | 5/2013 | van der Zanden et al. |
| 2014/0077874 | A1 | 3/2014 | Ahmed et al. |
| 2014/0114190 | A1 | 4/2014 | Chiang et al. |
| 2014/0184330 | A1 | 7/2014 | Dusad |
| 2014/0288428 | A1 | 9/2014 | Rothberg et al. |
| 2014/0293738 | A1 | 10/2014 | Yoshioka |
| 2015/0032002 | A1 | 1/2015 | Rothberg et al. |
| 2015/0091646 | A1 | 4/2015 | Shifrin |
| 2015/0280662 | A1 | 10/2015 | Nimran et al. |
| 2015/0297193 | A1 | 10/2015 | Rothberg et al. |
| 2015/0374335 | A1 | 12/2015 | Brown et al. |
| 2017/0160239 | A1 | 6/2017 | Chen et al. |
| 2018/0070925 | A1 | 3/2018 | Chen et al. |
| 2018/0364200 | A1 | 12/2018 | Chen et al. |

OTHER PUBLICATIONS

International Search Report and Written Opinion dated Mar. 27, 2017 in connection with International Application No. PCT/US2016/064322.

International Preliminary Report on Patentability dated Jun. 14, 2018 in connection with International Application No. PCT/US2016/064322.

International Search Report and Written Opinion dated Nov. 20, 2017 in connection with International Application No. PCT/US2017/049024.

Agarwal et al., Single-Chip Solution for Ultrasound Imaging Systems: Initial Results. 2007 IEEE Ultrasonics Symposium. Oct. 1, 2007;1563-6.

Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.

Cheng et al., An Efficient Electrical Addressing Method Using Through-Wafer Vias for Two-Dimensional Ultrasonic Arrays. 2000 IEEE Ultrasonics Symposium. 2000;2:1179-82.

Cheng et al., CMUT-in-CMOS ultrasonic transducer arrays with on-chip electronics. Transducers 2009. IEEE. Jun. 21, 2009;1222-5.

Cheng et al., Electrical Through-Wafer Interconnects with Sub-PicoFarad Parasitic Capacitance. 2001 Microelectromechan Syst Conf. Aug. 24, 2001;18-21.

Daft et al., 5F-3 A Matrix Transducer Design with Improved Image Quality and Acquisition Rate. 2007 IEEE Ultrasonics Symposium. Oct. 1, 2007;411-5.

Daft et al., Microfabricated Ultrasonic Transducers Monolithically Integrated with High Voltage Electronics. 2004 IEEE Ultrasonics Symposium. Aug. 23, 2004;1:493-6.

Gurun et al., Front-end CMOS electronics for monolithic integration with CMUT arrays: circuit design and initial experimental results. Proc Ultrason Symp. 2008;390-3.

Jiajian, Time-Gain-Compensation Amplifier for Ultrasonic Echo Signal Processing. Electronics Instrumentation Laboratory, Department of Microelectronics. Delft University of Technology. Feb. 2010 81 pages.

Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.

Kim et al., Design and Test of a Fully Controllable 64x128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

Tang et al., Automatic Time Gain Compensation in Ultrasound Imaging System. 3rd International Conference on Bioinformatics and Biomedical Engineering. Jun. 11-13, 2009. 4 pages.

* cited by examiner

ANALOG-TO-DIGITAL DRIVE CIRCUITRY HAVING BUILT-IN TIME GAIN COMPENSATION FUNCTIONALITY FOR ULTRASOUND APPLICATIONS

CROSS-REFERENCE TO RELATED APPLICATIONS

This Application is a continuation claiming the benefit under 35 U.S.C. § 120 of U.S. application Ser. No. 15/263,939, filed Sep. 13, 2016, and entitled "ANALOG-TO-DIGITAL DRIVE CIRCUITRY HAVING BUILT-IN TIME GAIN COMPENSATION FUNCTIONALITY FOR ULTRASOUND APPLICATIONS," which is hereby incorporated herein by reference in its entirety.

BACKGROUND

The present disclosure relates to ultrasound devices. In particular, the present disclosure relates to analog-to-digital conversion (ADC) drive circuitry having built-in time gain compensation (TGC) functionality for ultrasound applications.

Ultrasound devices may be used to perform diagnostic imaging and/or treatment. Ultrasound imaging may be used to see internal soft tissue body structures, and to find a source of disease or to exclude any pathology. Ultrasound devices use sound waves with frequencies that are higher with respect to those audible to humans. Ultrasonic images are created by transmitting pulses of ultrasound into tissue using a probe. The sound waves are reflected off the tissue, with different tissues reflecting varying degrees of sound. These reflected sound waves may be converted to electrical signals, amplified, digitized, recorded and displayed as an image to the operator. The strength (amplitude) of the sound signal and the time it takes for the wave to travel through the body provide information used to produce an image.

Many different types of images can be formed using ultrasound devices. The images can be real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

In one embodiment, a time gain compensation (TGC) circuit for an ultrasound device includes a first amplifier having a first integrating capacitor; and a control circuit configured to generate a TGC control signal that controls an integration time of the first integrating capacitor, thereby controlling a gain of the first amplifier, the integration time comprising an amount of time an input signal is coupled to the first amplifier before the input signal is isolated from the first amplifier.

In another embodiment, an analog-to-digital converter (ADC) driver circuit for an ultrasound device includes a first amplifier having first and second integrating capacitors in a feedback configuration; and a control circuit configured to generate a time gain compensation (TGC) control signal that controls an integration time of the first and second integrating capacitors, thereby providing time gain compensation by controlling a gain of the first amplifier, the integration time comprising an amount of time that an input signal is coupled to the first amplifier before the input signal is isolated from the first amplifier.

In another embodiment, an ultrasound system includes a receive channel configured to receive electrical signals from an ultrasonic transducer; and an analog circuit block having an input coupled to the receive channel and an output coupled to an analog-to-digital converter (ADC), the analog circuit block further including an ADC driver circuit including a differential amplifier having first and second integrating capacitors in a feedback configuration; and a control circuit configured to generate a time gain compensation (TGC) control signal that controls an integration time of the first and second integrating capacitors, thereby providing time gain compensation by controlling a gain of the differential amplifier, the integration time comprising an amount of time that an input signal is coupled to the differential amplifier before the input signal is isolated from the differential amplifier.

BRIEF DESCRIPTION OF THE DRAWINGS

Various aspects and embodiments of the disclosed technology will be described with reference to the following Figures. It should be appreciated that the figures are not necessarily drawn to scale. Items appearing in multiple figures are indicated by the same reference number in all the figures in which they appear, and where.

DETAILED DESCRIPTION

The present disclosure recognizes that certain analog circuit components in an ultrasound receiver circuit such as an ADC driver the TGC circuit, and optionally an auto-zero block may advantageously be combined. Such functional combinations may provide one or more benefits such as, for example: reducing the number of circuit stages, providing better power performance, and/or providing finer time gain compensation control.

Aspects of the present disclosure relate to a TGC circuit for an ultrasound device and a control circuit configured to generate a TGC control signal that controls the integration time of an integrating capacitor of an amplifier (and thus the gain of the amplifier). The integration time is the amount of time an input signal is coupled to the amplifier before being isolated from the amplifier.

Embodiments of the present disclosure are described more fully hereinafter with reference to the accompanying drawings, in which some, but not all, embodiments of the present disclosure are shown. Indeed, the present disclosure can be embodied in many different forms and should not be construed as limited to the embodiments set forth herein. Rather, these embodiments are provided so that this disclosure clearly satisfies applicable legal requirements. Like numbers refer to like elements throughout. As used herein, the terms "approximately", "substantially," and "about" may be used to mean within ±20% of a target value in some embodiments.

Ultrasonic signals are attenuated as they pass through body tissues, and thus signals received from deeper tissues are attenuated more than signals received from near field tissues. In addition, reflected signals from the deeper tissues may take longer to reach the transducer than those reflected from the near field tissues. Because of this attenuation, later arriving echoes from deep layers may be expected to have smaller amplitudes with respect to earlier arriving echoes from superficial layers, even if the deep and superficial layers have the same echogenicity. If an ultrasound image were formed by using such "raw" returned echoes, the image would appear lighter in superficial layers and darker in deep layers. Accordingly, one way to address ultrasound attenuation is through the use of time gain compensation (TGC) circuitry, in which signal gain is increased as time passes from the emitted wave pulse. This correction makes equally echogenic tissues look the same in the resulting image even if they are located at different depths.

Figure 1:
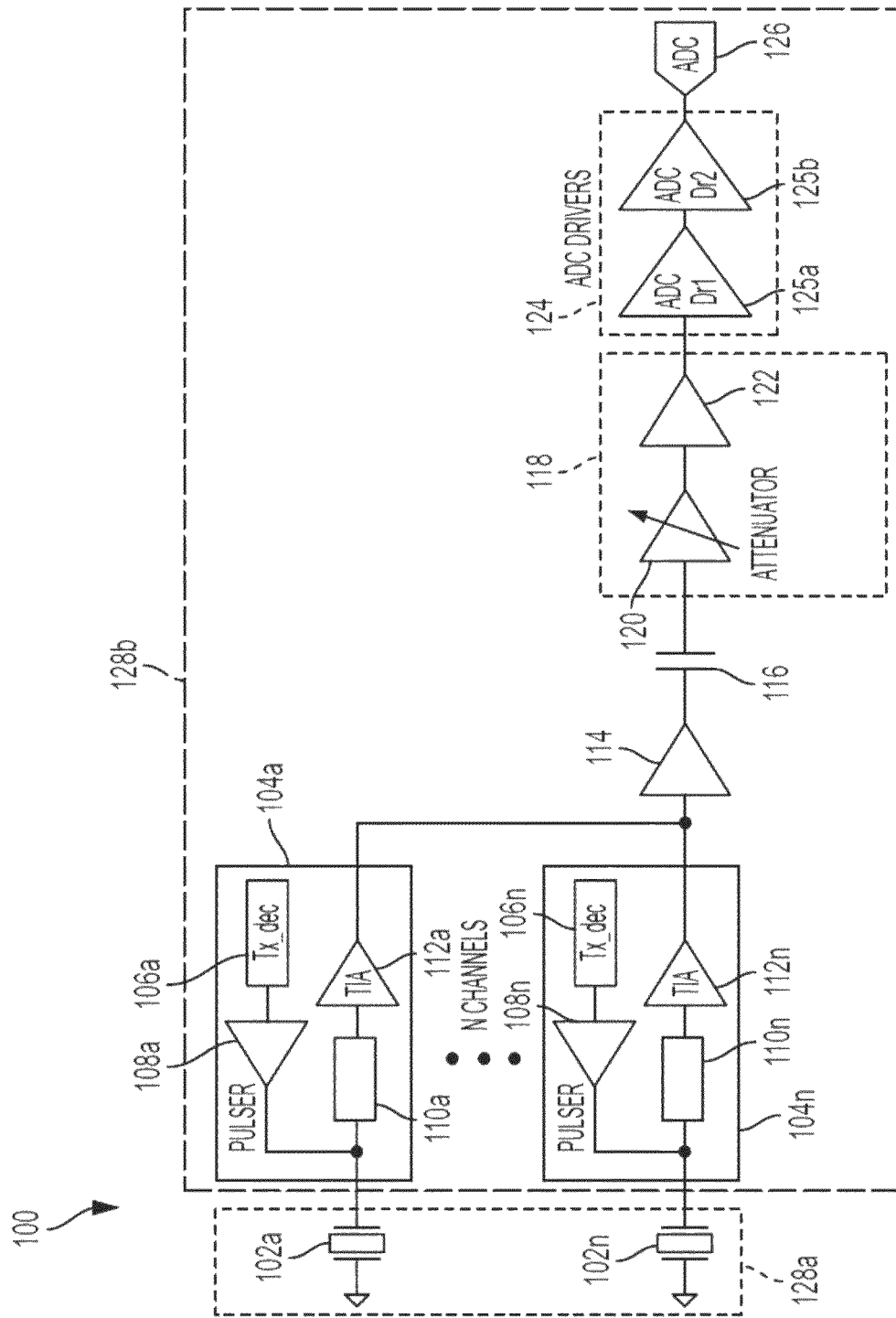
FIG. 1 is a schematic block diagram illustrating an exemplary circuit configured for transmitting and receiving ultrasound signals.

By way of further illustration, FIG. 1 is a schematic block diagram depicting an exemplary circuit 100 configured for processing received ultrasound signals. The circuit 100 includes N ultrasonic transducers 102a . . . 102n, wherein N is an integer. The ultrasonic transducers 102a-102n are sensors in some embodiments, producing electrical signals representing received ultrasound signals. The ultrasonic transducers 102a-102n may also transmit ultrasound signals in some embodiments. In addition, the ultrasonic transducers 102a-102n may be capacitive micromachined ultrasonic transducers (CMUTs) in some embodiments. In other embodiments, ultrasonic transducers 102a-102n may be piezoelectric micromachined ultrasonic transducers (PMUTs). Further alternative types of ultrasonic transducers may also be used in other embodiments.

As also illustrated in FIG. 1, the circuit 100 further includes circuitry channels 104a . . . 104n which may correspond to a respective ultrasonic transducer 102a . . . 102n. For example, there may be eight ultrasonic transducers 102a . . . 102n and eight corresponding circuitry channels 104a . . . 104n. In some embodiments, the number of ultrasonic transducers 102a . . . 102n may be greater than the number of circuitry channels 104a . . . 104n.

The circuitry channels 104a . . . 104n may include transmit circuitry, receive circuitry, or both. For example, the transmit circuitry may include transmit decoders 106a . . . 106n coupled to respective pulsers 108a . . . 108n. The pulsers 108a . . . 108n may control the respective ultrasonic transducers 102a . . . 102n to emit ultrasound signals. The receive circuitry of the circuitry channels 104a . . . 104n may receive the electrical signals output from respective ultrasonic transducers 102a . . . 102n. In the illustrated example, each circuitry channel 104a . . . 104n includes a respective receive switch 110a . . . 110n and an amplifier 112a . . . 112n. The receive switches 110a . . . 110n may be controlled to activate/deactivate readout of an electrical signal from a given ultrasonic transducer 102a . . . 102n. More generally, the receive switches 110a . . . 110n may be receive circuits, since alternatives to a switch may be employed to perform the same function. The amplifiers 112a . . . 112n may be trans-impedance amplifiers (TIAs).

The circuit 100 may also include an averaging circuit 114, which is also referred to herein as a summer or a summing amplifier. In some embodiments, the averaging circuit 114 is a buffer or an amplifier. The averaging circuit 114 may receive output signals from one or more of the amplifiers 112a . . . 112n and may provide an averaged output signal. The averaged output signal may be formed in part by adding or subtracting the signals from the various amplifiers 112a . . . 112n. The averaging circuit 114 may include, for example, a variable feedback resistance, the value of which may be adjusted dynamically based upon the number of amplifiers 112a . . . 112n from which the averaging circuit receives signals.

The averaging circuit 114 is coupled to an auto-zero block 116. Although not specifically depicted as such, the auto-zero block 116 receives a differential input signal and is used to sample and store any offset present on the differential pair. An output of the auto-zero block 116 is coupled to a time gain compensation (TGC) circuit 118 as discussed above. In the example shown, the TGC circuit 118 further includes a variable attenuator 120 and a fixed gain amplifier 122. An output of the TGC circuit 118 is coupled to an analog-to-digital converter (ADC) 126 via ADC drivers 124. In the illustrated example, the ADC drivers 124 include a first ADC driver 125a and a second ADC driver 125b. The ADC 126 digitizes the signal(s) from the averaging circuit 114.

In one embodiment, the ADC 126 may be a successive approximation register (SAR) ADC, which samples and holds an analog input voltage and implements a binary search algorithm using a multibit register (not shown). The multibit register is initialized to midscale, where the most significant bit (MSB) of the register is set to 1 and the remaining bits are set to 0. This in turn sets an internal digital-to-analog converter (DAC) output to be $V_{REF}/2$, where $V_{REF}$ (not shown) is a reference voltage provided to the ADC 126. A comparison is then performed to determine if the sampled input voltage $V_{IN}$ (not shown) is less than, or greater than the DAC output $V_{DAC}$ (not shown). If $V_{IN}$ is greater than $V_{DAC}$, the comparator output is a logic high, or 1, and the MSB of the multibit register remains at 1. Conversely, if $V_{IN}$ is less than $V_{DAC}$, the comparator output is a logic low and the MSB of the register is cleared to logic 0. The SAR control logic then moves to the next bit down, forces that bit high, and does another comparison. The sequence continues all the way down to the least significant bit (LSB). Once this is done, the conversion is complete and the digital word is available in the register.

It should be appreciated that various components illustrated in FIG. 1 may be located on a single substrate or on different substrates. For example, the ultrasonic transducers 102a . . . 102n may be on a first substrate 128a and the remaining illustrated components may be on a second substrate 128b. The first and/or second substrates 128a, 128b may be semiconductor substrates, such as silicon substrates. Alternatively, the components of FIG. 1 may be on a single substrate. For example, the ultrasonic transducers 102a . . .

102n and the illustrated circuitry may be monolithically integrated on the same semiconductor die. Such integration may be facilitated by using CMUTs as the ultrasonic transducers. Furthermore, the components of FIG. 1 form part of an ultrasound probe device. The ultrasound probe may, in one example, be handheld. In another example, the components of FIG. 1 form part of an ultrasound patch configured to be worn by a patient.

The present disclosure recognizes that certain components shown in FIG. 1 (and their respective functions), such as the ADC driver 124, the TGC circuit 118, and optionally the auto-zero block 116 may advantageously be combined. Such functional combinations may provide one or more benefits such as, for example: reducing the number of circuit stages, providing better power performance, and/or providing finer time gain compensation control.

Figure 2:
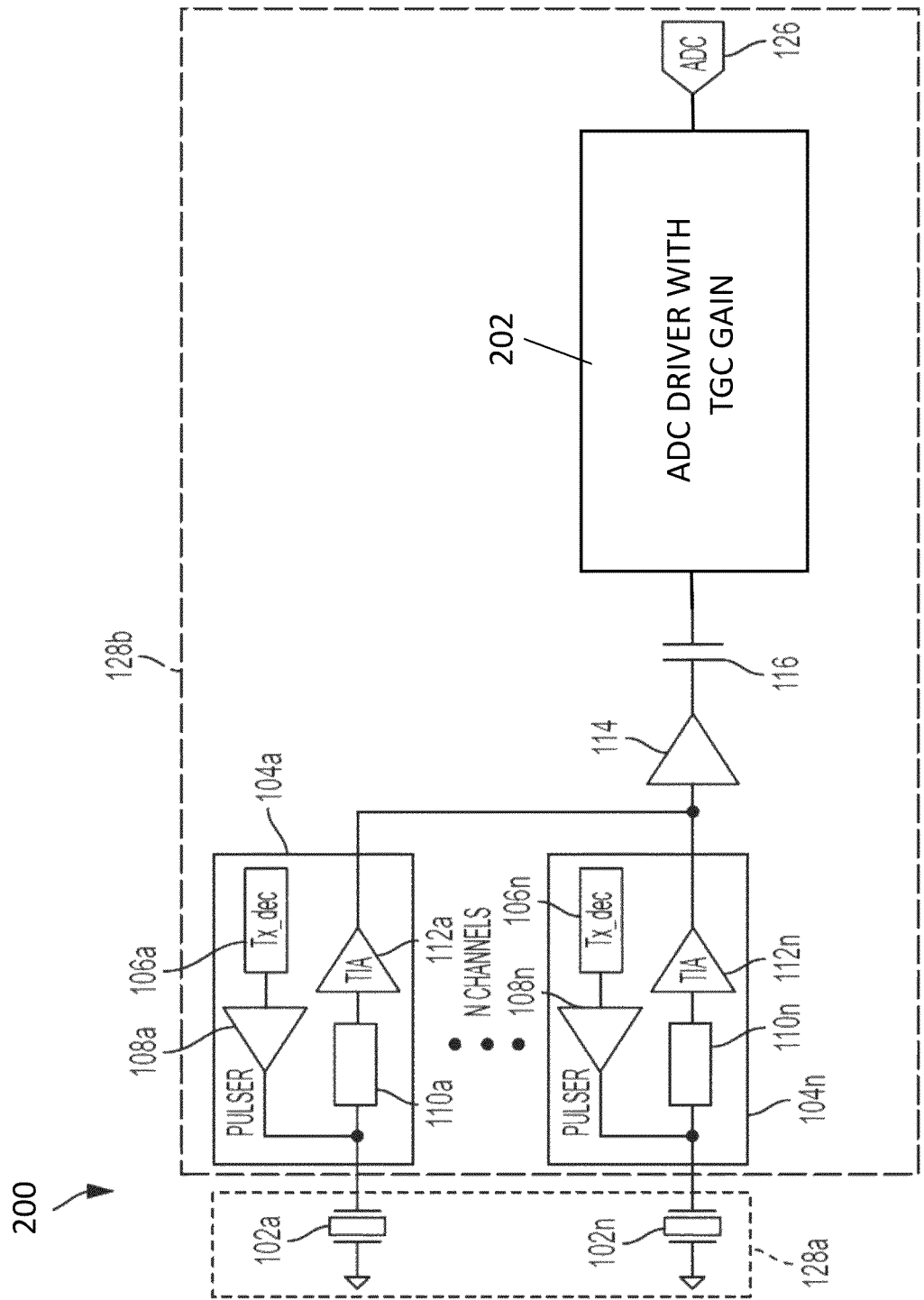
FIG. 2 is a schematic block diagram illustrating an exemplary circuit configured for transmitting and receiving ultrasound signals, according to an exemplary embodiment.

By way of further description, FIG. 2 is a schematic block diagram illustrating an exemplary circuit 200 configured for processing received ultrasound signals, according to a non-limiting embodiment of the present application. In comparison to FIG. 1, it will be seen that the circuit 200 of FIG. 2 replaces the individual TGC circuit 118 and ADC driver 124 with a single circuit block 202 representing an ADC driver having TGC gain functionality. One example of a circuit configuration for circuit block 202 is illustrated in FIG. 3.

Figure 3:
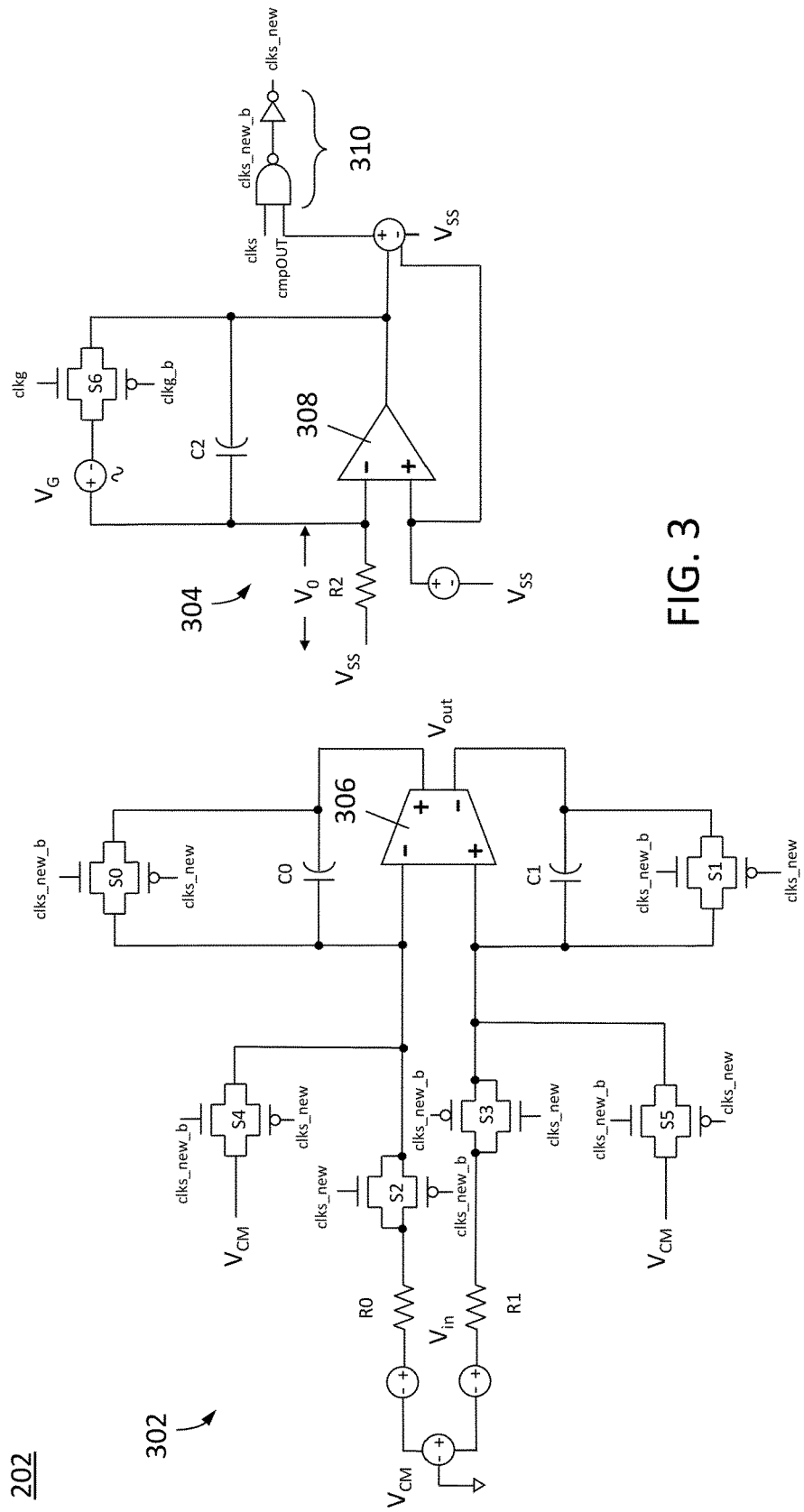
FIG. 3 is a schematic diagram of the ADC driver/TGC gain circuit block of FIG. 2.

As particularly shown in FIG. 3, the circuit block 202 includes an ADC driver circuit 302 and an auxiliary amplifier circuit 304. The ADC driver circuit 302 includes a fully differential integrating amplifier 306, integrating (gain) capacitors C0, C1, input resistors R0, R1, and NMOS/PMOS switches S0-S5. The auxiliary amplifier circuit 304 includes an operational amplifier 308, feedback capacitor C2, constant current resistor R2, NMOS/PMOS switch S6, and output clock logic 310.

The integrating capacitors C0 and C1 of the ADC driver circuit 302 provide time gain compensation, since the duration during which they integrate charge from the input signal may be varied. This varying integration time is based on an output clock signal (clks_new) generated by the auxiliary amplifier circuit 304. The output clock signal clks_new is in turn a function of a varying voltage gain control input signal, $V_G$, which is proportional to the desired gain provided by the TGC function.

In operation, the state of output clock signal clks_new is low during a reset phase (with its complementary signal clks_new_b being high), with a master sample clock signal clks (which is an input to clock logic 310) being held low. When clks_new is low during the reset phase, switches S2 and S3 of the ADC driver circuit are open, which decouples the differential input signal $V_{in}$ from the integrating amplifier 306. In addition, switches S0 and S5 are closed so as to clear charge on C0 and C1 and restore the amplifier 306 essentially to unity gain. Switches S4 and S5 are also closed in order to apply a common mode voltage ($V_{CM}$) to the inputs of the integrating amplifier 306.

During a sample phase, an input clock signal (clks) to the clock logic 310 will be high, which passes a comparator output signal (cmpOUT) of the auxiliary amplifier circuit 304 as the output clock signal clks_new. Initially, during the sample phase, cmpOUT is high, meaning that clks_new is also high. This results in switches S2 and S3 being closed, coupling the input signal $V_{IN}$ to the differential amplifier 306, and integrating the input signal onto capacitors C0 and C1 (with switches S0, S1, S4 and S5 being open). The amount of time that the input signal $V_{in}$ is allowed to integrate onto C0 and C1 (and thus the amount of gain provided by differential amplifier 306) depends on the amount of time switches S2 and S3 are closed, which in turn depends on the amount of time output clock signal clks_new remains high. In the auxiliary amplifier circuit 304, the variable voltage $V_G$ is applied across the capacitor C2 by closing switch S6 via an appropriate pulse of clock signal clkg and its complementary signal clkg_b. The state of cmpOUT (and hence the state of clks_new) flips from logic high to logic low after an amount of time proportional to the value of $V_G$. This amount of time, $T_{\_int}$, is given by the expression:

$$T_{\_int} = V_G \cdot (R_2 C_2)/V_0.$$

In turn, the integration time $T_{\_int}$ relates to an output gain for the input signal in accordance with the expression:

$$V_{out} = V_{in}/(R_0 C_0) \cdot T_{\_int} = (V_{in} \cdot V_G)/V_0 \cdot (R_2 C_2)/(R_0 C_0)$$

One observation to be made from the above expression (as well as an advantage of the present TGC topology embodiments) is the ratio of two RC time constants—the time constant of the RC network $R_2 C_2$ and the time constant of the RC network $R_0 C_0$. In semiconductor chip manufacturing, actual resistor and capacitor values may deviate from the desired design values due to fabrication imperfections. However, resistor and capacitor values for such components formed on the same chip may deviate in a consistent manner, meaning that a ratio between two resistors or between two capacitors can be made very accurate, even though each individual resistor value may be off. Here, because there is a ratio of resistors and capacitors in the TGC gain equation, the TUC gain may be accurately controlled, even in a case of electrical components having inaccurate values due to semiconductor fabrication processes.

Figure 4:
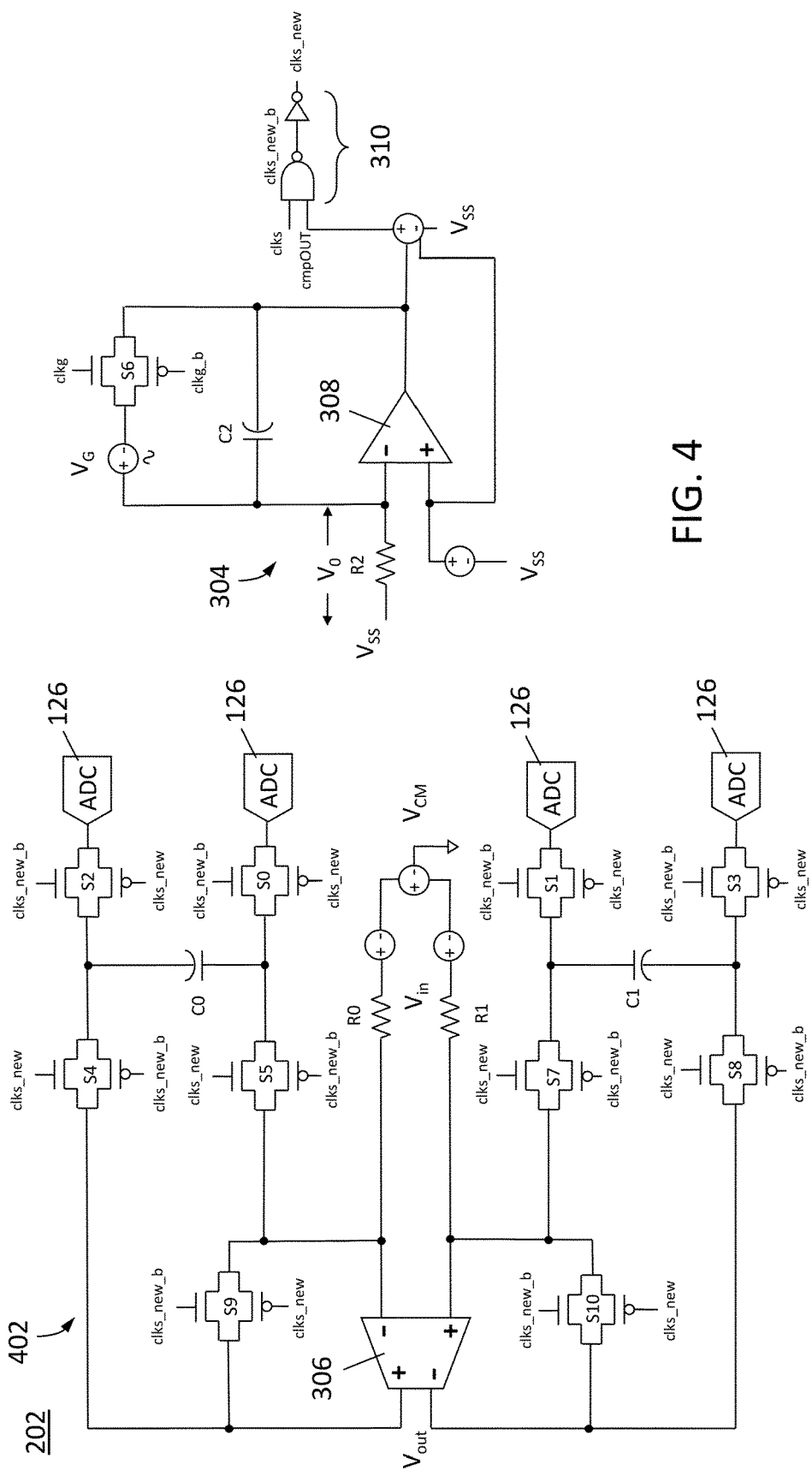
FIG. 4 is a schematic diagram of an alternative embodiment of the ADC driver/TGC gain circuit block of FIG. 2.

FIG. 4 illustrates an alternative topology 402 for the ADC driver circuit 302 of circuit block 200. In this embodiment, additional switches are used with respect to the embodiment of FIG. 3. As shown in FIG. 4, switches S0 and S2 are coupled to an SAR ADC stage 126 and discharge capacitor C0 by connecting both terminals to the common mode voltage $V_{CM}$ during the reset phase. Correspondingly, switches S1 and S3 discharge capacitor C1 by connecting both terminals to the common mode voltage $V_{CM}$ during the reset phase. In addition, switches S9 and S10 short circuit $V_{in}$ and $V_{out}$ during the reset phase. During sampling and integration, switches S4 and S5 allow the input signal $V_{in}$ to be integrated onto capacitor C0, while switches S7 and S8 allow the input signal $V_{in}$ to be integrated onto capacitor C1.

As will further be observed from the embodiment of FIG. 4, integrating capacitors C0 and C1 may also serve as sample and hold (S/H) capacitors for ADC inputs of an SAR ADC topology, in addition to providing time gain compensation. After the integration phase, switches S0/S2 and S1/S3 may be used to connect capacitors C0 and C1, respectively, via the SAR ADC stage 126 to perform the analog to digital conversion using the aforementioned SAR algorithm. After the end of each ADC conversion operation, capacitors C0 and C1 are reset to $V_{CM}$ and their respective charges cleared.

Figure 5:
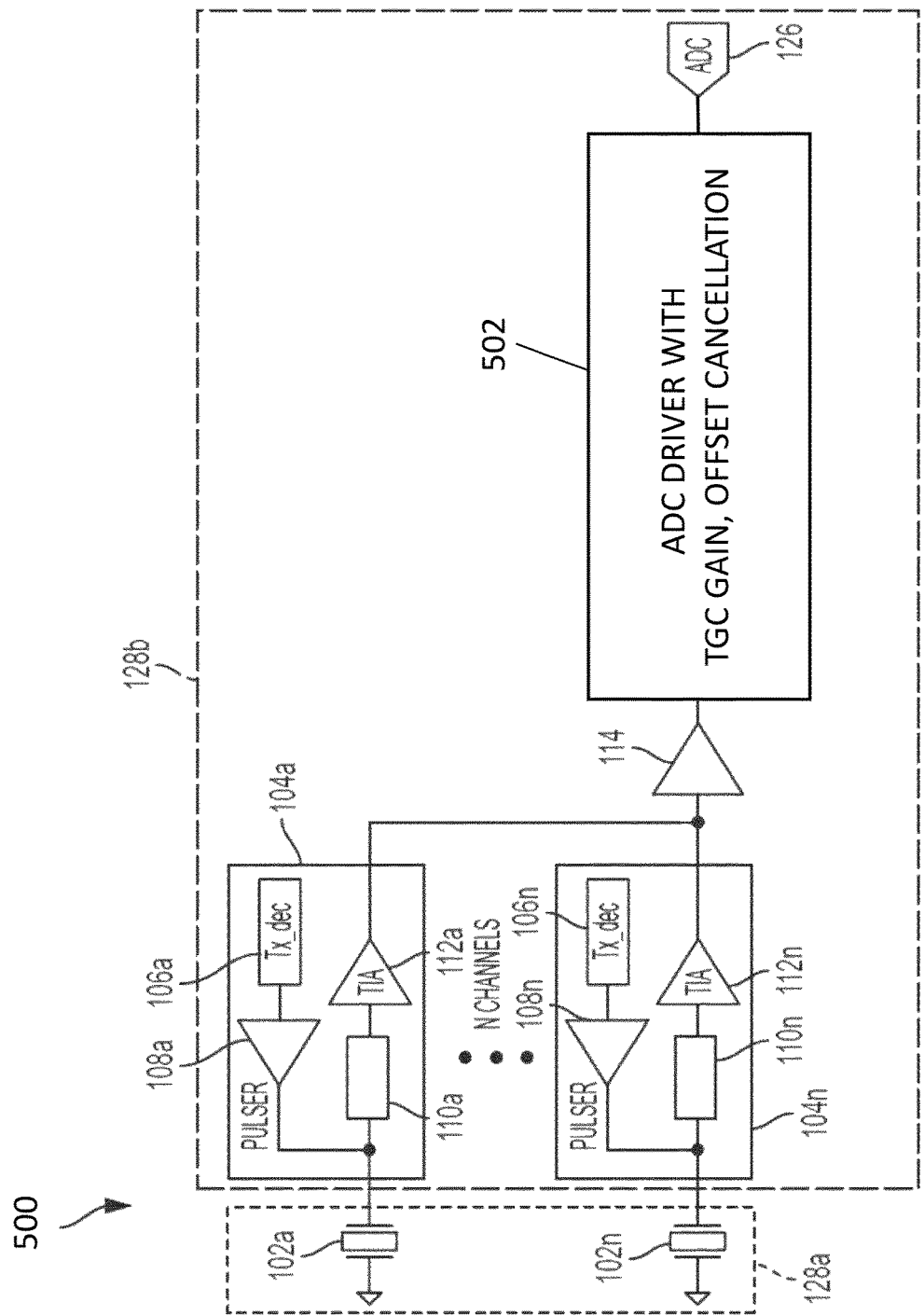
FIG. 5 is a schematic block diagram illustrating an exemplary circuit configured for transmitting and receiving ultrasound signals, according to another exemplary embodiment.

In addition to ADC driver and TGC functionality, alternative embodiments herein may also be used to further combine these features with zero-offset capability. Accordingly, FIG. 5 is a schematic block diagram illustrating an exemplary circuit 500 configured for processing received ultrasound signals, according to a non-limiting embodiment of the present application. In comparison to FIG. 1 and FIG. 2, it will be seen that the circuit 500 of FIG. 5 replaces the individual auto-zero block 116, TGC circuit 118 and ADC driver 124 with a single circuit block 502 representing an ADC driver having TGC gain and offset cancellation functionality.

Figure 6:
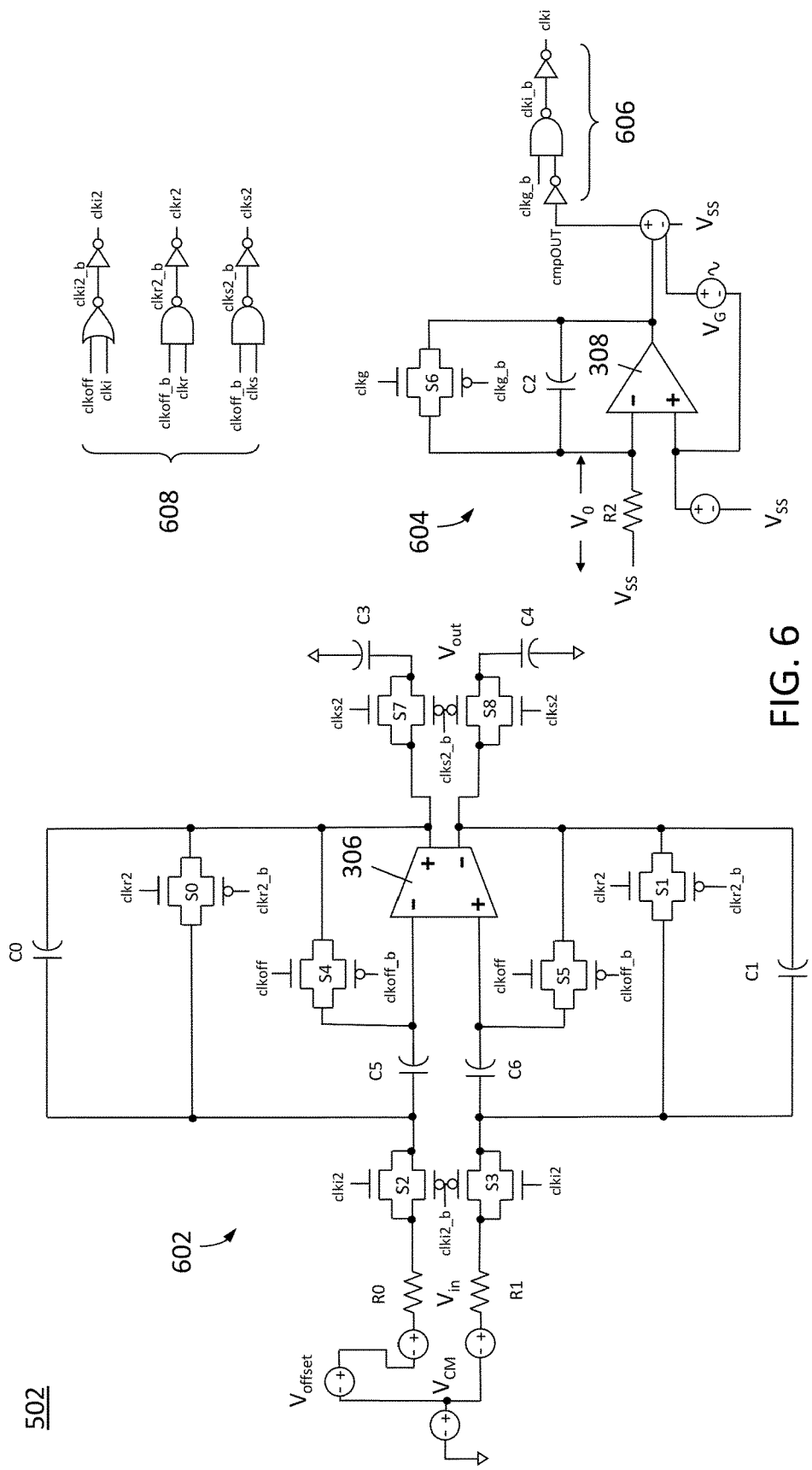
FIG. 6 is a schematic diagram of the ADC driver/TGC gain/offset cancellation circuit block of FIG. 5.

As more particularly shown in FIG. 6, circuit block 502 includes an ADC driver circuit 602 and an auxiliary amplifier circuit 604. For ease of description and comparison, embodiments having similar components are designated with like reference numerals. The ADC driver circuit 602 includes a fully differential integrating amplifier 306, integrating (gain) capacitors C0, C1, sample and hold capacitors C3, C4, offset voltage capacitors C5, C6, input resistors R0, R1, and NMOS/PMOS switches S0, S1, S2, S3, S4, S5, S7 and S8. The auxiliary amplifier circuit 604 includes an operational amplifier 308, feedback capacitor C2, constant current resistor R2, NMOS/PMOS switch S6, and output clock logic 606. As further shown in FIG. 5, clock logic 608 illustrates the generation of additional clock signals used by the ADC driver circuit 602 to implement ADC sample and hold functionality, TGC functionality, and offset cancellation (auto-zero) functionality. In comparison with the embodiments of FIG. 3 and FIG. 4, the integrating (gain) capacitors C0 and C1 are different than sample and hold capacitors C3 and C4, and may have smaller capacitance values than C3 and C4. This in turn allows for larger resistance values for R0 and R1, thus reducing power.

Figure 7:
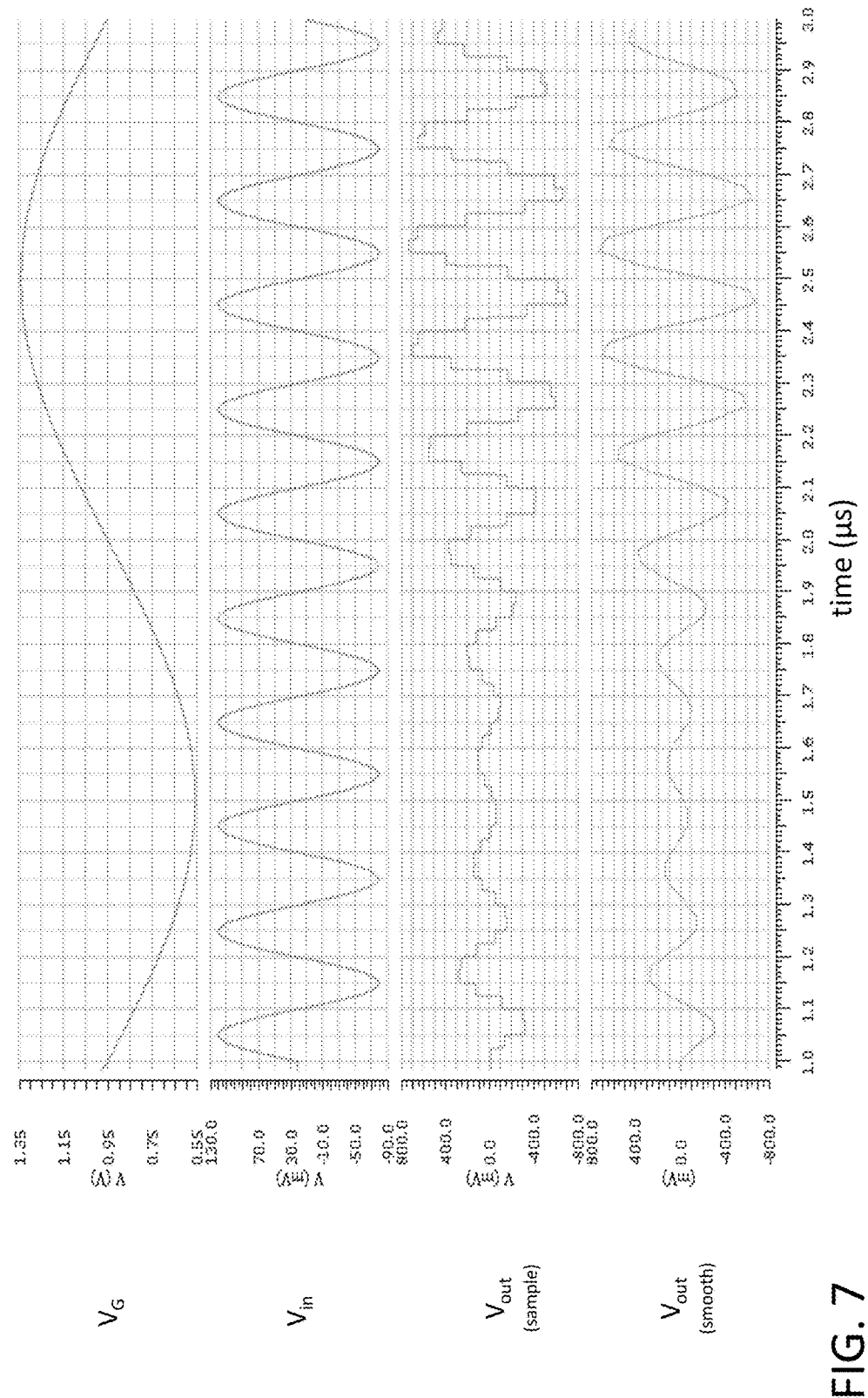
FIG. 7 is a series of waveform diagrams illustrating the relationship between a varying voltage signal, $V_G$, which is proportional to the desired gain provided by the TGC function, and the output of the ADC driver amplifier.

Referring now to FIG. 7, there is shown a series of waveform diagrams illustrating the TGC functionality provided by circuit block 502 in the embodiment of FIG. 6. It should be understood that the voltage levels and frequencies of the signals depicted in FIG. 7 are exemplary only, and may not necessarily correspond to an actual operation of receiving ultrasound signals. Rather, the exemplary waveforms depict example inputs to and outputs from the circuit block 500 for purposes of illustration. As shown, the uppermost waveform is the varying voltage $V_G$, which again is proportional to the desired TGC. In the example depicted, $V_G$ is a simple sinusoid wave oscillating at about 500 kHz, having a low value of about 0.55 volts (V) and a peak value of about 1.35 V. It will be noted that $V_G$ varies at a much slower rate with respect to the other signals. The waveform $V_{in}$ represents the value of the differential input signal received by circuit block 502, and is also a simple sinusoid of constant amplitude that oscillates at about 10× faster (i.e., 5 MHz) than $V_G$. $V_{out}$ (sample) is the resulting output value of the integrating amplifier 306, as seen at capacitors C3 and C4, and $V_{out}$ (smooth) is a smoothed version of $V_{out}$ (sample).

As will be noted from FIG. 7, the value of $V_G$ determines the amount of gain provided by the integrating amplifier 306 as seen at $V_{out}$. From about 1.0 μs to about 1.5 μs, $V_G$ decreases from a midrange value to a minimum value. Correspondingly, the resulting gain as seen by the amplitude of $V_{out}$ decreases to a minimum value. Subsequently, from about 1.5 μs to about 2.5 μs, $V_G$ transitions from the minimum value to a maximum value, which again is reflected by the gain of $V_{out}$ increasing from a minimum to a maximum value.

Figure 8:
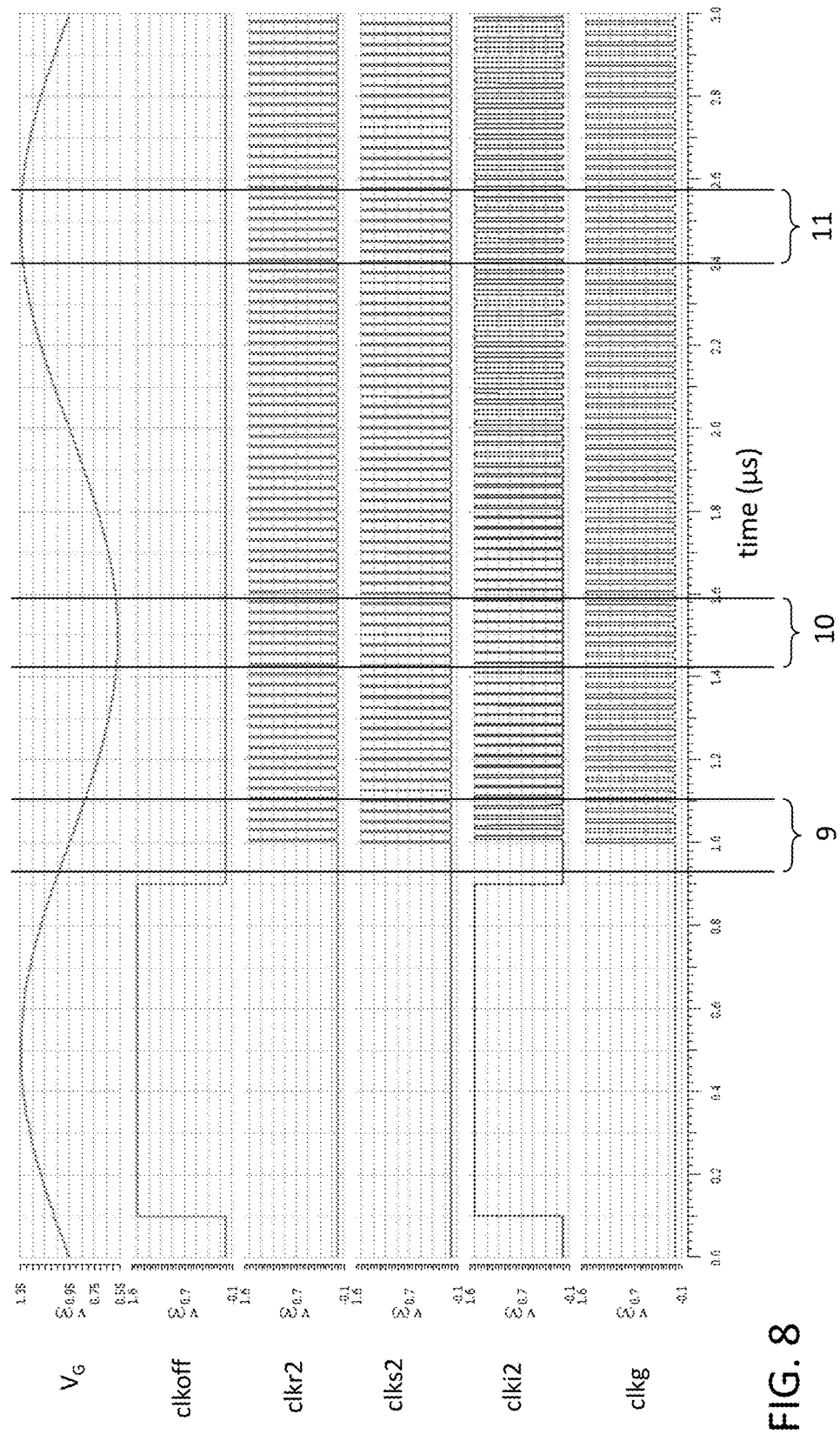
FIG. 8 is a series of waveform diagrams illustrating the relationship between the varying voltage signal, $V_G$, and various clock signals used to control the ADC driver amplifier.

For a further understanding of the operation of circuit block 502, reference may be made to the waveform diagrams in FIG. 8, which includes the TGC signal $V_G$, as well as various clock signals used by the ADC driver circuit 602 and the auxiliary amplifier circuit 604. More specifically, the clock signals include: clkoff and complementary signal clkoff_b (an input to clock logic 608 which controls the auto-zero offset cancellation function); clkr2 (a first output of clock logic 608 which controls reset of the TGC gain), clks2 and complementary signal clks2_b (a second output of clock logic 608 which controls the sample and hold function for the ADC input); clki2 and complementary signal clki2_b (a third output of clock logic 608 which controls integration time and thus TGC gain, and also works in conjunction with offset cancellation); and clkg (which controls operation of the auxiliary amplifier circuit 604 to ultimately generate clki2).

As shown in FIG. 8, the timing sequence begins with a relatively long offset cancellation (auto-zero) operation. This is reflected by clock signal clkoff going high for a duration of about 0.8 μs (e.g., from about 0.1 μs to about 0.9 μs, during which time there is no input differential signal present at the amplifier input. Rather, only the signal chain DC offset is present. As also illustrated by the clock logic 608 in FIG. 6, clkr2 and clks2 are both held low during the offset cancellation time period. That is, both input clock signals clkr and clks are gated off by the complementary clock signal (clkoff_b) of clkoff. In comparison, the OR logic included in clock logic 608 causes clock signal clki2 to be held high when clkoff is high. Clock signal clkg is also off during the offset period.

In terms of the ADC driver circuit 602, during the offset period switches S4 and S5 are closed, which equalizes the input and outputs of the integrating amplifier 306. Concurrently, switches S2 and S3 are closed, which couples $V_{in}$ to capacitors C5 and C6. Any offset voltage present (represented by $V_{offset}$ in FIG. 6) will be captured by a difference in voltage on C5 and C6, and during the offset reset phase, there is no input differential AC signal present.

It will be noted that the offset cancellation phase is only performed once before the ultrasound receiving phase, and the offset voltage is sampled and stored in capacitors C5 and C6 throughout the whole ultrasound receiving period (typically about 50–200 μs). In order to prevent sampling of any AC signal during this period (which may otherwise contribute to error in the offset cancellation), controls may be implemented from a higher level in the overall system control sequence to disconnect the ultrasonic transducers from the analog chain, such that only the DC offset is sampled without any AC signal in.

At the end of the offset cancellation period, clkoff goes low, which allows sampling of input signals to begin, incorporating TGC. Due to the relative high speed of the clock signals with respect to the 3.0 μs time scale in FIG. 8, certain portions of the overall sequence labeled by time segments 9, 10 and 11 are shown in greater detail in subsequent figures.

Figure 9:
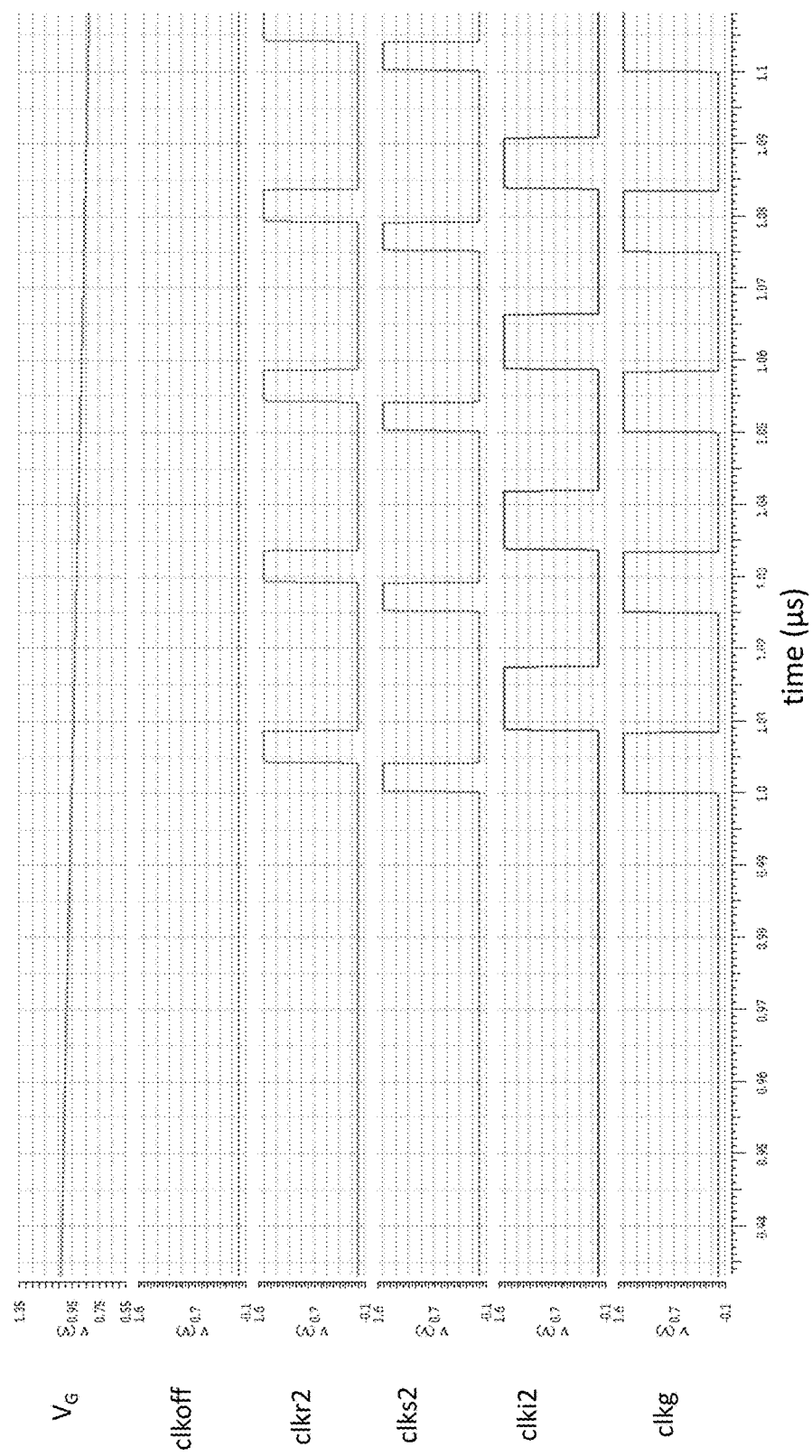
FIG. 9 illustrates the portion of the sequence represented by time segment 9 of FIG. 8.

Referring to FIG. 9, the timing diagram depicts the portion of the sequence represented by time segment 9 of FIG. 8. This period of time covers the beginning of the data sampling and reset period post-offset cancellation, at about 1.0 μs, when clkg initially pulses high. The duration of the clkg pulse (about 8 ns) coincides with a sample clock pulse by clks2 (about 4 ns) immediately followed by a reset clock pulse by clkr2 (also about 4 ns). So long as clkg is high, capacitor C2 of the auxiliary amplifier circuit 604 is discharged, which holds the output voltage of operational amplifier 308 below the value of $V_G$. As a result, the comparator output signal cmpOUT is held low. Since the output clock logic 606 uses clkg_b as a gating signal, clki (and consequently clki2) is held low during sampling and reset. Once clkg turns off, the comparator output signal cmpOUT is allowed to propagate through output clock logic 606, being inverted high at clki.

Thus, immediately after a sample and reset operation, S2 and S3 close to couple the input signal $V_{in}$ to the integrating amplifier 306. Since clkr2 and clks2 are also off when clkg goes low, switches S0 and S1 open to allow current to be integrated onto C0 and C1, and switches S7 and S8 open to decouple sample capacitors C3 and C4 from the output of integrating amplifier 306.

Another effect of clkg turning off is to allow current to begin charging capacitor C2 of the auxiliary amplifier circuit 604, which causes the output voltage of operational amplifier 308 to increase. Once this output voltage exceeds the threshold compare value as set by $V_G$, cmpOUT will change state from low to high, which in turn causes clki and clki2 to switch low and discontinue integration on capacitors C0 and C1. The time taken to reach this threshold compare value is again dependent upon the magnitude of $V_G$, in accordance with the expression:

$$T\_int = V_G \cdot (R_2 C_2)/V_0;$$

with the output gain for the input signal given by:

$$V_{out} = V_{in}/(R_0 C_0) \cdot T\_int = (V_{in} \cdot V_G)/V_0 \cdot (R_2 C_2)/(R_0 C_0)$$

The ratio of the two RC time constants $(R_2 C_2)/(R_0 C_0)$ may be set as desired to achieve a desired gain range. In one exemplary embodiment, the ratio of $(R_2 C_2)/(R_0 C_0)$ may be about 5; however, other values are also contemplated.

In the specific time segment shown in FIG. 9, the value of $V_G$ is at about a midpoint with respect to its maximum and minimum values, and decreasing. Consequently, the on-time of clki2 in this segment (about 8 ns) is roughly half the available amount of total integration time allowed by the off duration of clkg (e.g., about 16 ns). Once clkg pulses high, C2 is discharged, clki2 turns off to isolate the input signal $V_{in}$ from integrating amplifier 306. Clks2 then pulses to capture the output on C3 and C4, followed by clkr2 pulsing high to discharge C0 and C1 thereby resetting the integrating amplifier 306 to unity gain.

Figure 10:
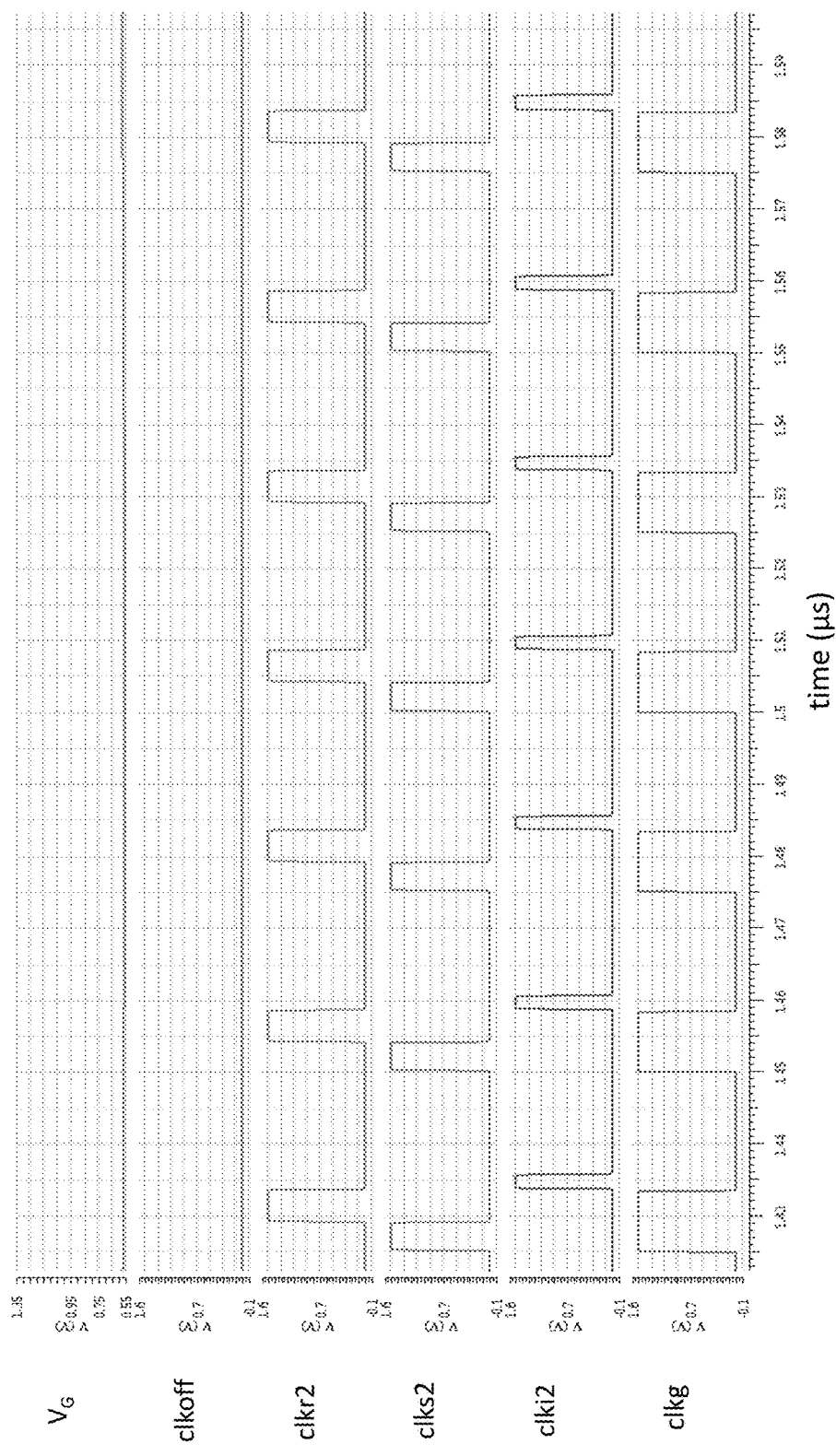
FIG. 10 illustrates the portion of the sequence represented by time segment 10 of FIG. 8.

Referring now to FIG. 10, the timing diagram illustrates the time segment 10 of FIG. 8, which occurs from about 1.42 μs to about 1.60 μs. This segment corresponds to a time period where $V_G$ is at a minimum value. When $V_G$ is at a minimum, the integration time T_int is also at a minimum, meaning that clki2 has the shortest clock pulse. As shown in FIG. 10, clki2 has a pulse duration of about 2 ns, corresponding to the smallest TGC value provided by the ADC driver circuit 602.

Figure 11:
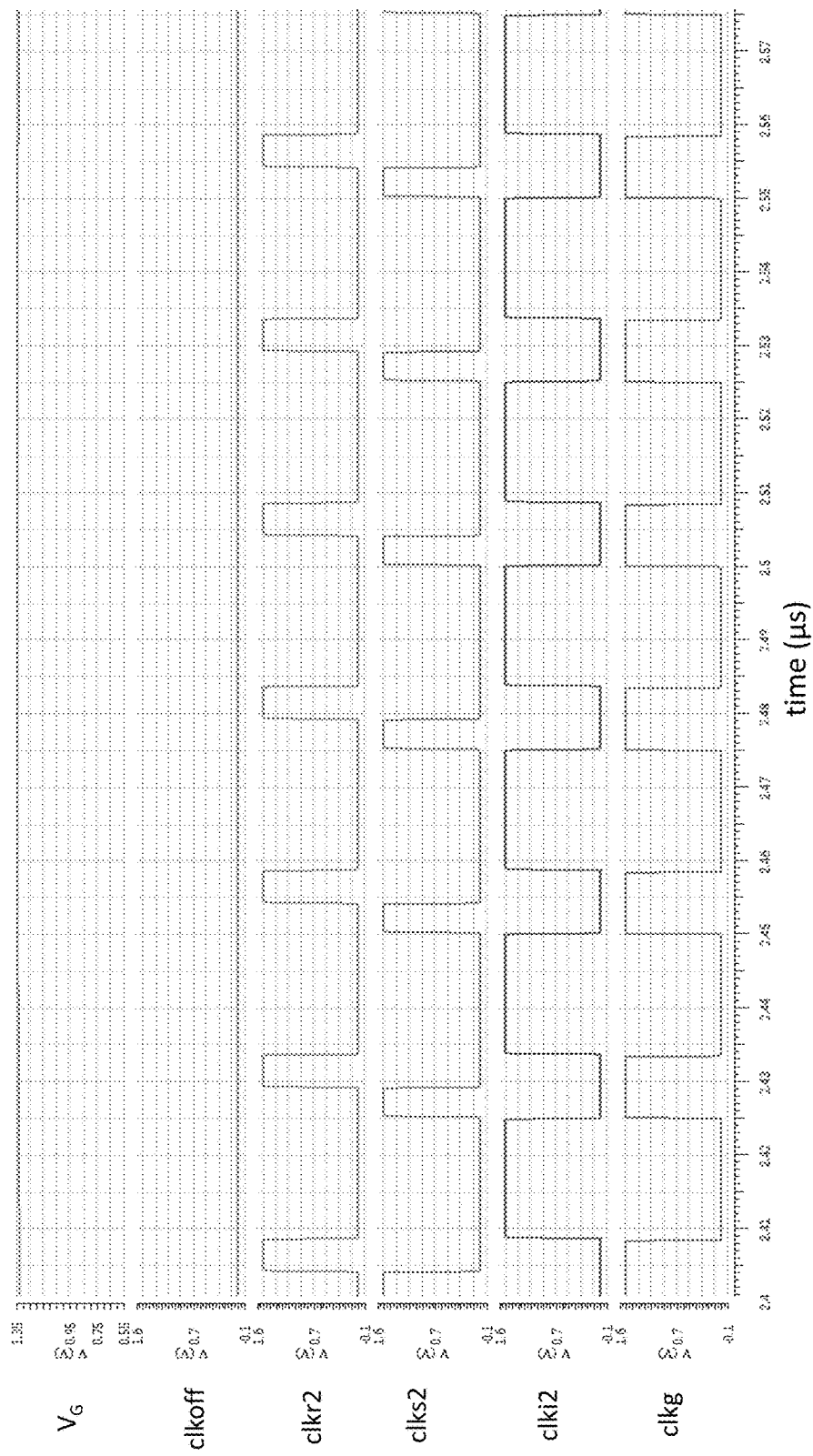
FIG. 11 illustrates the portion of the sequence represented by time segment 11 of FIG. 8.

By way of comparison, the timing diagram of FIG. 11 illustrates the time segment 11 of FIG. 8, which occurs from about 2.40 μs to about 2.58 μs. This segment corresponds to a time period where $V_G$ is at a maximum value. When $V_G$ is at a maximum, the integration time T_int is also at a maximum, meaning that clki2 has its longest clock pulse duration. As shown in FIG. 11, the pulse duration of clki2 corresponds to the entire time of the off duration of clkg, resulting in the largest TGC value provided by the ADC driver circuit 602. Here, it is possible for $V_G$ to be large enough such that the state of cmpOUT does not flip prior to clkg going high. In this case, it would actually be the transition of clkg going high that gates off clki2.

As will thus be appreciated, embodiments of a TGC amplifier, which integrates and amplifies an input signal according to control signals generated from an auxiliary amplifier are disclosed. The input signal to the TGC amplifier is a continuous analog signal, operated based on a sampling clock. The amplifier outputs are discrete time analog voltage samples stored on capacitors, where the analog voltage is the amplified version of the input signal amplitude, having a gain proportional to a TGC control voltage. Prior to generating each sample, the TGC amplifier resets to clear the previous charge stored on its capacitors.

The TGC amplifier is then configured into an integrating amplifier which integrates the input signal onto the capacitors, until to the point when the auxiliary amplifier trips a threshold. The integrating time, T_int, is proportional to a gain control input signal, $V_G$, and as a result the input signal is amplified up by a value proportional to $V_G$.

Discrete time analog voltage samples stored on capacitors may be directly coupled to an ADC, such that the analog voltage samples are turned into digital words. In this sense, a TGC amplifier may serves as an ADC driver at the same time. Furthermore, the offset cancellation functionality may be implemented in the TGC amplifier, which cancels not only the offset from the fully differential TGC amplifier, but all the upstream offsets coming from analog front-end amplifiers preceding the TGC stage.

It should also be appreciated that although the integrating amplifier 306 is described as a fully differential amplifier in the embodiments illustrated, it can also be implemented as a single-ended amplifier in other embodiments. Conversely, while the operational amplifier 308 of the auxiliary amplifier circuit 304 is described as a single-ended amplifier, it may also be implemented as a differential amplifier in other embodiments.

The techniques described herein are exemplary, and should not be construed as implying any particular limitation on the present disclosure. It should be understood that various alternatives, combinations and modifications could be devised by those skilled in the art from the present disclosure. For example, steps associated with the processes described herein can be performed in any order, unless otherwise specified or dictated by the steps themselves. The present disclosure is intended to embrace all such alternatives, modifications and variances that fall within the scope of the appended claims.

What is claimed is:

1. A method of controlling gain in a time gain compensation (TGC) circuit for an ultrasound device, the method comprising:
   generating, by a control circuit, a TCG control signal to control an integration time of a first integrating capacitor of a first amplifier of the TGC circuit, the integration time comprising an amount of time an input signal is coupled to the first amplifier before the input signal is isolated from the first amplifier.

2. The method of claim 1, wherein the first amplifier comprises a differential amplifier.

3. The method of claim 2, wherein the differential amplifier comprises an analog-to-digital converter (ADC) driver.

4. The method of claim 1, further comprising generating the TGC control signal by comparing an output voltage of a second amplifier and a threshold voltage determined by a value of a variable gain control input signal, the second amplifier configured as a comparator circuit and having a feedback capacitor.

5. The method of claim 4, wherein the second amplifier comprises an operational amplifier.

6. The method of claim 1, wherein the integration time controlled by the TGC control signal is dependent upon an RC time constant of the control circuit and a voltage of the variable gain control input signal.

7. The method of claim 6, wherein an output gain of the first amplifier is proportional to a ratio between resistance and capacitance values of the control circuit and resistance and capacitance values of the first amplifier.

8. The method of claim 7, wherein the ratio is about 5.

9. The method of claim 1, wherein the first integrating capacitor also comprises a sample and hold capacitor of an analog-to-digital converter (ADC).

10. The method of claim 9, further comprising storing and cancelling an offset voltage associated with the input signal to the first amplifier, and storing and cancelling an offset voltage associated with the first amplifier itself.

11. A method of driving an analog-to-digital converter (ADC) circuit, the method comprising:
generating a time gain compensation (TGC) control signal that controls an integration time of first and second integrating capacitors of a first amplifier of an analog-to-digital converter (ADC) driver circuit for an ultrasound device; and
providing, with a control circuit, time gain compensation by controlling a gain of the first amplifier by generating the time gain compensation (TGC) control signal, wherein the integration time comprises an amount of time that an input signal is coupled to the first amplifier before the input signal is isolated from the first amplifier.

12. The method of claim 11, wherein the first amplifier comprises a differential amplifier.

13. The method of claim 12, further comprising selectively coupling a pair of ADC sample and hold capacitors to output terminals of the differential amplifier.

14. The method of claim 13, further comprising coupling a pair of offset voltage capacitors to input terminals of the differential amplifier.

15. The method of claim 14, further comprising:
discharging, with a first pair of switches, the first and second integrating capacitors during a reset mode of operation;
coupling, with a second pair of switches, the input signal to the differential amplifier following the reset mode of operation, and to thereafter isolating the input signal from the differential amplifier according to the TGC control signal;
coupling, with the second pair of switches, the input signal to the offset voltage capacitors during an offset cancellation mode of operation;
equalizing, with a third pair of switches, the input and output terminals of the differential amplifier during the offset cancellation mode; and
coupling, with a fourth pair of switches, the output terminals of the differential amplifier to the ADC sample and hold capacitors during a sample mode of operation.

16. The method of claim 11, further comprising generating the TGC control signal by comparing an output voltage of a second amplifier of the control circuit and a threshold voltage determined by a value of a variable gain control input signal, the second amplifier configured as a comparator circuit.

17. The method of claim 16, wherein the second amplifier comprises an operational amplifier.

18. The method of claim 17, wherein the integration time controlled by the TGC control signal is dependent upon an RC time constant and a voltage of the variable gain control input signal.

19. The method of claim 18, further comprising charging a feedback capacitor of the control circuit is charged with a constant current such that a state of the TGC control signal changes once the output voltage of the operational amplifier exceeds the threshold voltage determined by the variable gain control input signal.

20. The method of claim 19, further comprising selectively discharging the feedback capacitor.

21. A method of operating an ultrasound system, the method comprising:
receiving electrical signals from an ultrasonic transducer;
coupling the electrical signals to an input of an analog circuit block; and
coupling an output of the analog circuit block to an analog-to-digital converter (ADC), the analog circuit block further comprising:
an ADC driver circuit including a differential amplifier having first and second integrating capacitors configured in a feedback configuration; and a control circuit configured to provide time gain compensation by generating a time gain compensation (TGC) control signal that controls an integration time of the first and second integrating capacitors, the integration time comprising an amount of time that an input signal is coupled to the differential amplifier before the input signal is isolated from the differential amplifier.

22. The method of claim 21, further comprising:
selectively coupling a pair of ADC sample and hold capacitors to output terminals of the differential amplifier, the differential amplifier having a pair of offset voltage capacitors coupled to input terminals of the differential amplifier;
discharging, with a first pair of switches, the first and second integrating capacitors during a reset mode of operation;
coupling, with a second pair of switches, the input signal to the differential amplifier following the reset mode of operation, and thereafter isolating the input signal from the differential amplifier according to the TGC control signal, and coupling the input signal to the offset voltage capacitors during an offset cancellation mode of operation;
equalizing, with a third pair of switches, the input and output terminals of the differential amplifier during the offset cancellation mode; and
coupling, with a fourth pair of switches, the output terminals of the differential amplifier to the ADC sample and hold capacitors during a sample mode of operation.

23. The method of claim 22, further comprising generating the TGC control signal by comparing an output voltage of an operational amplifier of the control circuit with a threshold voltage determined by a value of a variable gain control input signal, the operational amplifier having a feedback capacitor.

24. The method of claim 23, wherein the integration time controlled by the TGC control signal is dependent upon a capacitance of the feedback capacitor and a voltage of the variable gain control input signal.

25. The method of claim 24, further comprising charging the feedback capacitor of the control circuit with a constant current such that a state of the TGC control signal changes once the output voltage of the operational amplifier exceeds the threshold voltage determined by the variable gain control input signal.

26. The method of claim 25, further comprising selectively discharging the feedback capacitor with a switch of the control circuit.

27. The method of claim 21, wherein the first and second integrating capacitors also serve as a pair of ADC sample and hold capacitors.

28. The method of claim 27, further comprising:
discharging, with a first pair of switches, the first and second integrating capacitors during a reset mode of operation;
coupling, with a second pair of switches, the input signal to the differential amplifier following the reset mode of operation, and thereafter isolating the input signal from the differential amplifier according to the TGC control signal; and
coupling, with a third pair of switches, a common mode voltage to input and output terminals of the differential amplifier during the reset mode.

29. The method of claim 27, further comprising:
discharging, with a first pair of switches, the first integrating capacitor during a reset mode of operation;
discharging, with a second pair of switches, a second integrating capacitor during the reset mode of operation;
equalizing, with a third pair of switches, the input and output terminals of the differential amplifier during the reset mode of operation; and
coupling, with a fourth pair of switches, the first integrating capacitor to the input and output terminals of the differential amplifier following the reset mode of operation.

30. The method of claim 27, further comprising:
generating the TGC control signal by comparing an output voltage of an operational amplifier and a threshold voltage determined by a value of a variable gain control input signal, the operational amplifier having a feedback capacitor;
wherein the integration time controlled by the TGC control signal is dependent upon an RC time constant of the control circuit and a voltage of the variable gain control input signal.

\* \* \* \* \*